(12) United States Patent
Hiraga

(10) Patent No.: US 6,331,818 B1
(45) Date of Patent: Dec. 18, 2001

(54) HUMAN BODY DETECTING DEVICE AND METHOD THEREFOR

(75) Inventor: Tetsuo Hiraga, Tokushima (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/647,242

(22) PCT Filed: Jan. 25, 2000

(86) PCT No.: PCT/JP00/00366

§ 371 Date: Nov. 30, 2000

§ 102(e) Date: Nov. 30, 2000

(87) PCT Pub. No.: WO00/45355

PCT Pub. Date: Aug. 3, 2000

(30) Foreign Application Priority Data

Jan. 29, 1999 (JP) .................................................. 11-022746

(51) Int. Cl.⁷ .................................................. G08B 23/00
(52) U.S. Cl. .................................... 340/573.1; 340/573.7; 340/575; 600/558
(58) Field of Search ........................... 340/573.1, 573.4, 340/573.7, 575; 600/301, 322, 532, 558

(56) References Cited

U.S. PATENT DOCUMENTS

| | | | |
|---|---|---|---|
| 4,916,435 | * | 4/1990 | Fuller .................. 340/573.4 |
| 5,335,180 | * | 8/1994 | Tahajashi et al. .................. 701/117 |
| 5,573,006 | * | 11/1996 | Shimotani et al. .................. 340/575 |
| 5,795,306 | * | 8/1998 | Shimotani et al. .................. 600/558 |
| 5,800,360 | * | 9/1998 | Kisner et al. .................. 600/532 |

FOREIGN PATENT DOCUMENTS

| | | |
|---|---|---|
| 8-69523 | 3/1996 | (JP) . |
| 8-287383 | 11/1996 | (JP) . |
| 8-293075 | 11/1996 | (JP) . |
| 9-16876 | 1/1997 | (JP) . |
| 9-50529 | 2/1997 | (JP) . |
| 10-234030 | 9/1998 | (JP) . |

* cited by examiner

Primary Examiner—Van Trieu
(74) Attorney, Agent, or Firm—Wenderoth, Lind & Ponack, L.L.P.

(57) ABSTRACT

The present invention confirms whether a caregiven person, such as a solitary advanced aged person, is living a normal daily life, while respecting the privacy when the caregiven person is in a normal state. The present invention further outputs a detailed video with a warning to a caregiver when the caregiven person has fallen into an abnormal state. A human body detecting device comprises an imaging unit, a human body detecting unit for detecting a human body from an image signal obtained from the imaging unit, a state judging unit for judging a state of the human body, and a normal/abnormal signal outputting unit, a field memory for storing the image signal, a second memory for dividing a pixel data of the human body included in the image signal into blocks of a predetermined number of pixels and luminance, to be stored, and a selector for selectively performing a reading out from the field memory for storing the image signal and from the second memory in accordance with the judgement of the state judging unit, wherein the reading out from the field memory is authorized only when it is judged that abnormal states are encountered by the state judging unit.

12 Claims, 3 Drawing Sheets

A

HUMAN BODY DETECTING DEVICE AND METHOD THEREFOR

TECHNICAL FIELD

The present invention relates to a human body detecting unit and a human body detecting method for processing an image imaged by a camera, thereby to detect a presence of a human body, and notify abnormalities in actions of a human body.

BACKGROUND ART

In recent years, the population of advanced-aged persons has increased. Further, care for solitary advance-aged persons have been socially required. Therefore, use of human body detecting devices have increased as life sensors for seeing whether solitary advanced-aged people live daily lives in good health.

One prior art human body detecting device is an infrared sensor, which detects differences between extreme infrared radiation energies radiated from backgrounds such as indoor walls, floors, and ceilings or the like, and extreme infrared radiation energies radiated from a human body, so as to output a detection signal. Such infrared sensors are mainly utilized for prevention of crimes, and control of indoor illuminations and a ventilation fans.

In addition, another one employs a television camera, for prevention of crimes. This system reproduces a video signal from a television camera, that is positioned in an area to be monitored, on a monitor in a monitoring place; so as to monitor the area. Since a human body detecting device employing a television camera enables a user to see with his eyes, the area to be monitored as it is, the device has an advantage that a direction of the television camera is facilitated.

The above-described prior art human body detecting devices have the following problems.

At first, an infrared sensor type human body detecting device detects a radiated energy fluctuation amount, i.e., a change in a heat quantity, which results in a difficulty in directing the same to the area to be monitored. Next, it is constructed such that a detection signal is output during a predetermined period when an action of the human body is detected. Therefore, when a human body comes to a standstill after it has been detected, and such a standstill state continues beyond a predetermined period, the device fails to output a detection signal. More particularly, the detection state has come to be in an abnormal state, and therefore, the person in the standstill state cannot be detected.

Further, in a human body detecting device employing a television camera, the area to be monitored can be seen with eyes as it is, which results in a difficulty in adapting such a device to a place where a privacy should be respected.

Further, in order to protect a privacy, it might be considered to superimpose noise into the video signal so as to make the video difficult to be seen on a caregiver side. However it is impossible to provide a detailed video information to the caregiver when a caregiven person has fallen into an abnormal state.

Further, from the view of a protecting privacy, as described in Japanese Published Patent No. Hei. 10-234030, it might be considered that an original image captured by the television camera is transmitted from the caregiven person side to the caregiver side, and when the original image is analyzed on the caregiver side, and a predetermined state can be met, the original image is output on the monitor television provided on the caregiver side. However, in this method, the original image is always transmitted to the caregiver side. As such, a device provided on the caregiver side can be intentionally altered so as to output the original image on the monitor television. Further, since an analyzing means for the original image is provided to the caregiver, the original image should be regularly transmitted from the caregiven person's house to the caregiver's house via a public circuit network or the like, which results in requiring a large amount of communication expenses.

The present invention is made to solve the above-described problems. It is an object of the invention to provide a human body detecting device which can be adapted to a place where privacy is respected, such as a toilet or a bathroom, and can be used as a life sensor for seeing whether a person is in good health, and can provide more detailed video information to the caregiver at a distant place when detecting abnormalities in the human body.

DISCLOSURE OF THE INVENTION

In order to realize the above-described objects, according to the present invention, a human body detecting device comprises: an imaging unit; a human body detecting unit for detecting a human body from an image signal obtained by the imagine unit; a state judging unit for judging a state of the human body; a normal/warning signal outputting unit for outputting a normal signal or a warning signal dependent on whether the human body is in a normal state or in an abnormal state; said human body detecting device comprises: a field memory for storing the image signal; a second memory for dividing an image data of a human body portion included in the image signal into blocks of a predetermined number of pixels and luminance, to be stored; and a selection means for selectively performing, a reading out from the field memory and from the second memory in accordance with a judgement result of the state judging unit; wherein the selection means selects to authorize a reading out from the field memory only when it is judged that abnormal states are encountered in the human body by the state judging unit.

Thus, when a human body is detected, an image signal in which a human body portion is divided into blocks of a predetermined number of pixels and luminance is output from the second memory. When abnormalities in the human body are detected, an image signal is output from the field memory. Therefore, a reading out from the field memory is authorized so that the image signal is output as a video signal only when abnormal states are encountered in the human body. Accordingly, when a caregiven person normally lives a daily life, privacy can be secured. When a human body is in an abnormal state such as a case where the caregiven person falls down and becomes motionless, a detailed video signal can be transmitted to the caregiver. Therefore, it is possible to provide useful information for nursing activities as well as providing an efficient information for confirming whether or not the provided information is wrong. Further, when the caregiven person normally lives a daily life, a video signal is transmitted to the caregiver side once a day or several times a day, whereby it is possible to confirm that the caregiven person is normally living a daily life on the caregiver side, and communication expenses of a public circuit can be sharply reduced.

Further, according to the present invention, in the human body detecting device, the human body detecting device comprises: a switch for authorizing a transmission of the image data from the field memory selected by the selection means; and a contact and communication means for contacting to urge to push the switch.

Thus, in response to a call from the caregiver in a caregiving center at a distant place receiving a warning, signal notifying abnormalities in the human body, a detailed video signal can be voluntarily transmitted by the caregiven persons whereby privacy can be protected even more.

Further, according to the present invention, a human body detecting method comprises: an imaging unit; a human body detecting unit for detecting a human body from an image signal obtained by the imaging unit; a state judging unit for judging a state of the human body; a normal/warning signal outputting unit for Outputting a normal signal or a warning signal dependent on whether the human body is in a normal state or in an abnormal state; said human body detecting method comprises: a field memory for storing the image signal; a second memory for dividing an image data of a human body portion included in the image signal into blocks of a predetermined number of pixels and luminance, to be stored; and a selection means for selectively performing a reading out from the field memory and from the second memory in accordance with a judgement result of the state judging unit; and the selection means selects to authorize a reading out from the field memory only when it is judged that abnormal states are encountered by the state judging unit.

Thus, when a human body is detected, an image signal in which a human body portion is blocked into blocks of a predetermined number of pixels and luminance is output from the second memory. When abnormalities in the human body are detected, an image signal is output from the field memory. Therefore, a reading out from the field memory is authorized so as to be output as a video signal only when abnormal states are encountered in the human body. Accordingly, when a caregiven person normally lives a daily life, a privacy can be secured. When a human body is in an abnormal state such as a case where the caregiven person falls down and becomes motionless, a detailed video signal can be transmitted to the caregiver. Therefore, it is possible to provide useful information for nursing activities as well as providing efficient information for confirming whether or not the provided information is wrong. Further, when the caregiven person normally lives a daily life, a video signal is transmitted to the caregiving side once a day or several times a day, whereby it is possible to confirm that the caregiven person is living a normal daily life on the caregiver side, and communication expenses of a public circuit can be sharply reduced.

Further, according to the present invention, in the human body detecting method comprises: a switch for authorizing a transmission of the image data from the field memory selected by the selection means; and a contact and communication means for contacting to urge to push the switch.

Thus, in response to a call from a caregiver in a caregiving center at a distant place receiving a warning signal notifying abnormalities in the human body, a detailed video signal can be voluntarily transmitted by the caregiven person, whereby privacy can be protected even more.

BEST MODE FOR CARRYING OUT THE INVENTION

[Embodiment 1]

Hereinafter, a first embodiment of the present invention corresponding to embodiments of the present invention will be described with reference to FIG. 1.

Figure 1:
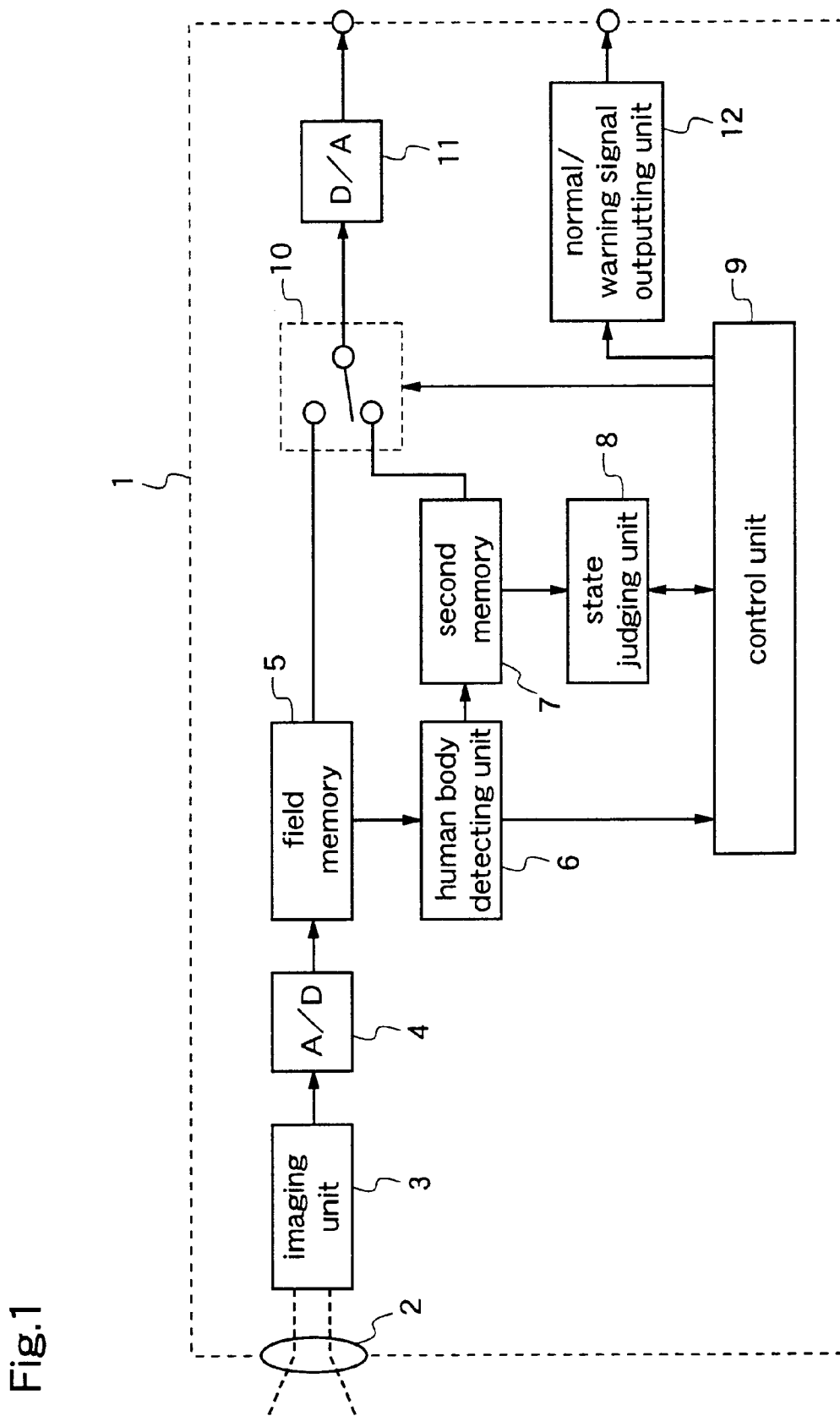
FIG. 1 is a block diagram illustrating a human body detecting device according to a first embodiment of the present invention.

FIG. 1 is a block diagram illustrating a human body detecting device according to the first embodiment of the present invention.

In FIG. 1, reference numeral 2 designates an imaging lens. Numeral 3 designates an imaging unit comprising a CCD (Charged Coupled Device) element for converting an image captured and formed by the imaging lens 2 to an electrical signal, and a video signal processing circuit. Numeral 4 designates an A/D converter for converting an analog signal to a digital signal. Numeral 5 designates a field memory. Numeral 6 designates a human body detecting unit for extracting characteristics of a human body from an image signal, detecting a human body portion, and dividing pixel data of a human body portion into blocks of a predetermined number of pixels and luminance level. Numeral 7 designates a second memory for storing the blocked data. Numeral 8 designates a state judging unit for judging that a human body is in a normal life state or in an abnormal life state from data stored in the second memory 7. Numeral 9 designates a control circuit for: judging whether an output of a warning signal should be issued in accordance with a signal from the human body detecting unit 6 showing whether a human body is detected and a signal from the state judging unit 8 showing whether a human body is in a normal state or in an abnormal state; outputting a selection signal controlling to switch memories (the field memory 5 or the second memory 7), from which image data should be read out; and outputting an instruction signal to issue an output of a normal signal when the human body is judged to be in the normal state, or outputting an instruction signal to issue a warning signal when the human body is judged to be in the abnormal state. Numeral 10 designates a selection means for alternatively switching in accordance with the selection signal so that detailed image data is output from the field memory 5 in the abnormal state, or blocked image data is output from the second memory 7 in the normal state. Numeral 11 designates a D/A converter for converting image data selected by the selection means 10 to an analog video signal. Numeral 12 designates a normal/warning signal outputting unit for outputting, a normal signal or a warning signal to the outside in accordance with the instruction signal output from the control unit 9.

Hereinafter, an operation of the human body detecting device 1 is described with reference to FIGS. 1 and 3

In FIG. 1, the imaging lens 2 forms an image of a front view in the imaging unit 3. The imaging unit 3 converts the formed-image to an electrical signal as an image signal. The A/D converter 4 converts the image signal output from the imaging unit 3 to digital data, so as to store the same as image data in the field memory 5. Image data are successively renewed with the image signal from the imaging unit 3.

The human body detecting unit 6 transmits, without processing, the image data in the field memory 5 to the second memory 7, so as to be stored in the second memory 7 when the image data stored in the field memory 5 is analyzed to find that no human body can be detected. Further, when the human body is detected, the human body detecting unit 6 converts and divides pixel data of the human body portion into blocks of pixel data having uniformed luminance as defining a predetermined pixel number as one block as shown in FIG. 3, so as to be transmitted and stored in the second memory 7, as well as, notifying to the control unit 9 that a human body is detected. With reference to a human body detecting method from the image data, there is a method for grasping a change in an image so as to extract and detect a shape of a human body from characteristics of the shape of the human body, and methods as described in Japanese Published Patent Application No. Hei. 8-69523 and No. Hei. 9-50529.

The control unit 9 receives a signal notifying that the human body is detected, from the human body detecting unit 6, and outputs an instruction signal instructing to judge a state of the human body to the state judging unit 8. The state judging unit 8 receives the instruction signal to judge the state of the human body from the control unit 9, judges whether the human body is in a normal state from the image data of the second memory 7, and returns the result to the control unit 9. In order to judge whether the human body is in an abnormal state, there are methods of judging whether the person is in an abnormal state, such as being down when there are changes in the data of the human body portion in the second memory 7 during a predetermined period, or a method as described in Japanese Published Patent Application No. Hei. 9-50529.

In accordance with the result of judgement as to whether the human body is in an abnormal state from the state judging unit 8, the control unit 9 makes the selection means 10 connect with the second memory 7 when the human body is not in the abnormal state, i.e., it is in the normal state, whereas the control unit 9 makes the selection means 10 switch to the field memory 5 when the human body is in the abnormal state. Thereby, the image data stored in the respective memories are output to the D/A converter 11. The D/A converter 11 converts the image data that is selected and input to an analog video signal, so that such analog video signal is output to the outside.

Further, also in case where the judgement as to whether the human body is in an abnormal state by the state judging unit 8 shows that the human body is in an abnormal state, the image data which is not divided into blocks stored in the side of the field memory 5 can be output, whereby, it is possible to confirm a precise state.

In addition, the control unit 9 receives a signal from the human body detecting unit 6 indicating that the human body is detected. The control unit 9 then judges whether the person is living a normal daily life when the judgement result as to whether the human body is in an abnormal state does not indicate that the human body is in an abnormal state. The control unit 9 then outputs a normal signal to the normal/warning, signal output unit 12 indicating that the caregiven person is living a normal daily life. Further, the control unit 9 receives a signal from the human body detecting unit 6 indicating that a human body is detected. The control unit 9 then judges whether the person has fallen into an abnormal state when the judgement result as to whether the human body is in an abnormal state indicates that the person is in an abnormal state. Consequently, a warning signal is output from the normal/warning signal output unit 12.

As described above, according to the human body detecting device and the human body detecting method of this first embodiment, the image signal of the caregiven person obtained by the imaging lens is divided into blocks of a predetermined pixel number and luminance, the image data of the human body is detected from the blocked pixel signal, and a state of the detected image data is judged by the state judging unit. When the person is in the normal state, a normal signal is output. When the caregiven person has some abnormalities in the body, a warning signal is output so as to output the blocked image data of the human body. Therefore, it is possible to establish the device in a place where a privacy is respected, such as a toilet or a bathroom, and appropriately notify the abnormal state in the human body of the care given person to the caregiver. In addition, it is possible to accurately confirm whether the information is wrong.

[Embodiment 2]

Next, a second embodiment of the present invention corresponding to claims 2 and 4 of the present invention will be described with reference to FIG. 2.

Figure 2:
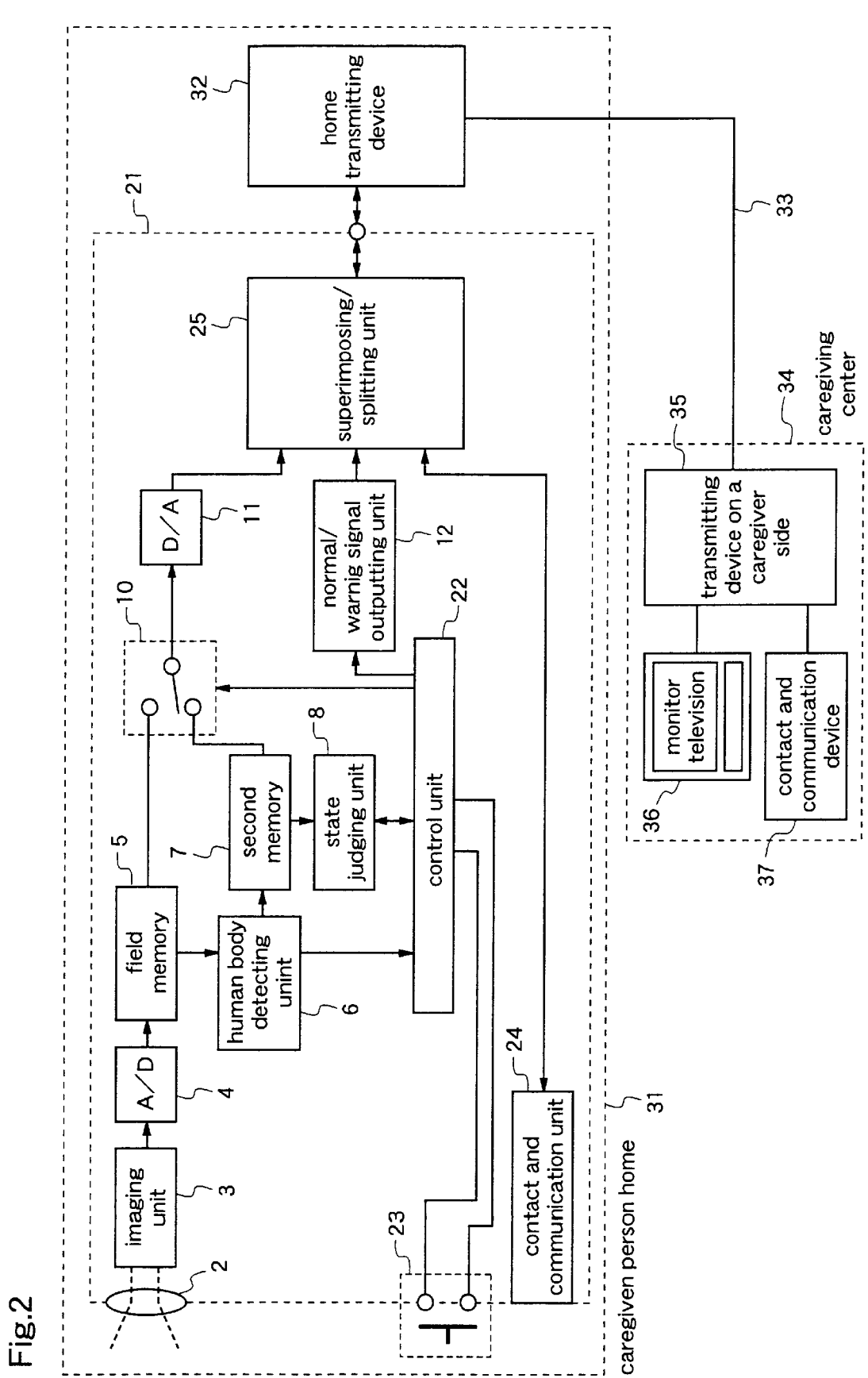
FIG. 2 is a system block diagram illustrating a warning system employing a human body detecting device according to a second embodiment of the present invention.

FIG. 2 is a system block view illustrating a warning system employing a human body detecting device according to the second embodiment of the present invention.

In FIG. 2, an imaging lens 2, an imaging unit 3 an A/D converter 4, a field memory 5, a human body detecting unit 6, a second memory 7, a state judging unit 8, a selecting means 10, a D/A converter 11, and a normal/warning signal outputting unit 12 in a human body detecting device 21 according to this second embodiment have same structures to those in the human body detecting device 1 according to the first embodiment.

Further, the human body detecting device 21 according to the second embodiment comprises an authorizing switch 23 for authorizing to transmit a detailed video signal when a human body is in an abnormal state, a contact and communication unit 24 for contacting and communicating with a caregiving center at a distant place, a control unit 22, a superimposing/splitting unit 25 for superimposing/splitting a video signal output from the D/A converter 11, a normal signal or a warning signal output from the normal/warning signal outputting unit 12, and a contact and communication signal provided for contacting or communicating in order to save connected wirings between transmitting devices such as a modem device or the like, for transmitting various signals from the human body detecting device 21 and the human body detecting device 21 according to the second embodiment to the caregiving center 34.

Further, the human body detecting device 21 constructed as described above is connected to a home transmitting device 32 having functions for transmitting to the outside a normal signal indicating that the person is living a normal daily life, or a warning signal indicating the person has fallen into an abnormal state, the video signal, and the contact and communication signal via a public circuit network 33 to a caregiving center 34 at a distant place, as well as receiving a contact and communication signal from the caregiving center 34.

The caregiving center 34 comprises a transmitting device on a caregiver side for receiving the normal signal indicating that the caregiven person is living a normal daily life, or the warning signal indicating that the human body has fallen into an abnormal state, the video signal, and the contact and communication signal transmitted via the public circuit network 33, as well as for transmitting the contact and communication signal. The caregiving center further comprises a contact and communication device 37 for contacting and communicating to a caregiven person home 31 when the body is in an abnormal state, and a monitor television 36.

Hereinafter, an operation of the above-described human body detecting device 21 will be described with referring to FIGS. 2 and 3.

Explanations of operations of the imaging lens 2, the image unit 3, the A/D converter 4, and the field memory 5 are omitted since the operations are the same as described in the first embodiment.

Figure 3:
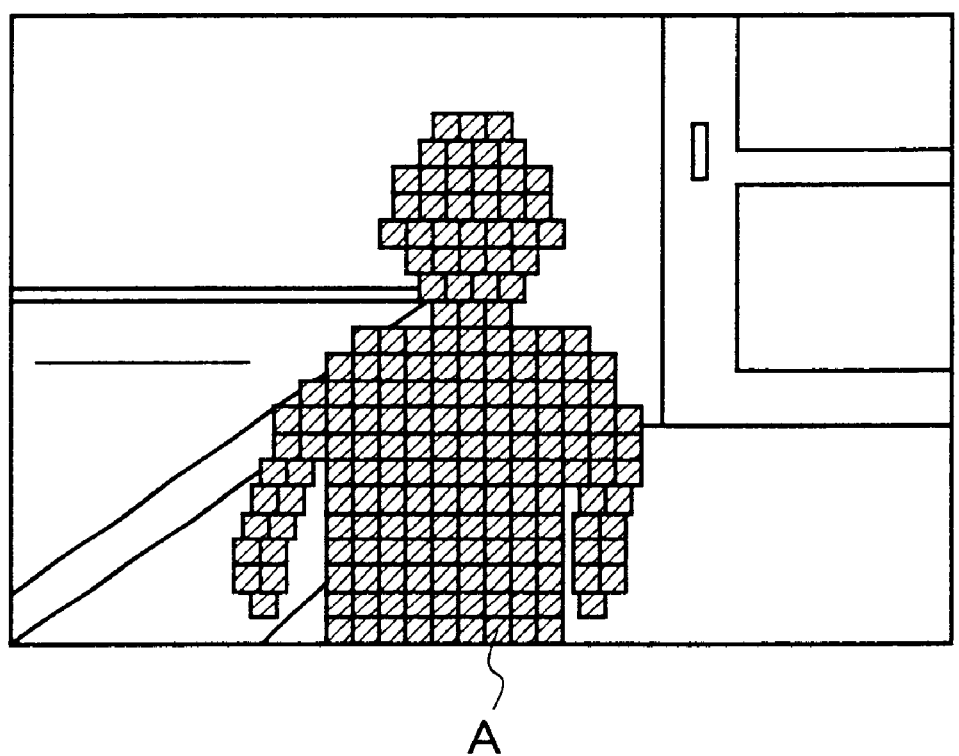
FIG. 3 is a view illustrating a blocked human body according to the first and the second embodiments of the present invention.

In FIG. 2, when a human body is detected in the image data in the field memory 5, the human body detecting unit 6, similarly as described in the first embodiment, divides image data of the human body portion into blocks of a predetermined number of pixels as shown in FIG. 3, converts the same to pixel data having uniformed luminance, and stores the same in the field memory 5, as well as outputting a human body detecting signal to the control unit 22.

The control unit 22, similarly as described in the first embodiment, receives the human body detecting signal, and outputs an instruction signal to judge a state of the human body to the state judging unit 8. The state judging unit 8 receives the instruction signal to judge the state of the human body from the control unit 22, judges whether the human body is in an abnormal state in accordance with the image data from the second memory 7, and returns the result to the control unit 22.

In accordance with the judgement result as to whether the human body is in an abnormal state from the state judging unit 8, the control unit 22 determines that the person is living a normal daily life when the judgement result does not show and abnormal state, and outputs a normal signal showing that the caregiven person is living a normal daily life from the normal/warning signal outputting unit 12. At this time, since the selection means 10 selects the second memory 7, the image data in the second memory 7 is converted to a video signal in D/A converter 11 to be input in the superimposing/splitting unit 25. The normal signal and the video signal input in the superimposing/splitting unit 25 are superimposed, output to the outside of the human body detecting device 21, and transmitted to the transmitting, device on the caregiver side 35 provided on the caregiving center 34 via the home transmitting device 32 and the public circuit network 33.

The transmitting device on the caregiver side 35 can confirm that the caregiven person is living a normal daily life in accordance with the received normal signal as well as outputting the video signal on the monitor television 36. Further, with respect to a transmission of the normal signal from the human body detecting device 21, a frequency of confirmation as to whether caregiven person is living a normal daily life can be arbitrarily set, such as once a day, in accordance with a setting of the control unit 21.

Further, when the judgement result as to whether the human body is in an abnormal state from the state judging unit 8 shows that the body is in an abnormal state, the control unit 22 outputs a warning signal from the normal/warning signal outputting unit 12, as well as starting the contact and communication unit 24. At this time, unlike the first embodiment, the selection means 10 is constructed to select not the field memory 5 but the second memory 7, whereby the image data in the second memory 7 are converted to a video signal in the D/A converter 11 so as to be input in the superimposing/splitting unit 25. The warning signal, the video signal, and an audio signal from the contact and communication unit 24 input in the superimposing/splitting unit 25 are superimposed, output to the outside of the human body detecting device 21, and transmitted to the transmitting device on the caregiver side 35 provided on the caregiving center 34 via the home transmitting device 39 and the public circuit network 33.

The transmitting device on the caregiver side 35 recognizes that the caregiven person has some abnormalities in accordance with the received warning signal, and notifies the caregiver in the caregiving center 34 by a warning sound or the like that abnormal states are encountered, as well as outputting the video signal on the monitor television 36. Since the video signal is formed from the image data in the second memory 7 provided on the human body detecting device 21, the human body portion of the video output on the monitor television 36 is a blocked video having a uniformed luminance.

In case where the caregiver wishes to know more detailed state by the video, when the caregiver in the caregiving center 34 calls the caregiven person by the contact and communication device 37, the audio signal reaches to the contact and communication unit 24 provided on the human body detecting device 21 via the transmitting device on the caregiver side 35, the public circuit network 33, and the home transmitting device 32. And then, the same is output as a sound, and transmitted to the caregiven person, thereby enabling a conversation. Therefore, the caregiver asks the caregiven person to push the authorizing switch 23.

When the caregiven person pushes the authorizing switch 23, the control unit 22 detects that the authorizing switch 23 is switched, and switches the selection means 10 so as to select the field memory 5. As a result, the image data stored in the selected field memory 5 are converted to a video signal in the D/A converter 11, to be input in the superimposing/splitting unit 25. The video signal is superimposed together with the warning signal and the audio signal in the superimposing/splitting unit 25, and output to the outside of the human body detecting device 21, and input in the transmitting device on the caregiver side 35 via the home transmitting device 32 and the public circuit network 33, so that the transmitting device on the caregiver side 35 outputs the video signal on the monitor television 36. Since the video signal output on the monitor television 36 is formed from the image data stored in the field memory 35 provided on the human body detecting device 21. Therefore, it is a detailed video signal imaged by the imaging unit 3, and it is easier to be understood compared with the blocked image signal formed by the image data in the second memory 7.

The authorizing switch 23 provided on the human body detecting device 21 can employ a wireless pendant-type switch so that the caregiven person can wear it around the neck, whereby the caregiven person in an abnormal state can easily push the authorizing switch 23. Further, a receiving unit for receiving a wireless signal indicating when the wireless pendant-type switch is pushed may be provided in the human body detecting device 21.

According to the human body detecting device and the human body detecting method of the second embodiment of the present invention, an image signal of the caregiven person obtained by the imaging lens is divided into blocks of a predetermined number of pixels and luminance, the image data of the human body is detected from the blocked pixel signal, and a state of the detected image data is judged by the state judging unit. When the caregiven person is in a normal state, a normal signal is output. When the caregiven person has some abnormalities in the human body, a warning signal is output. Further, when the warning signal is output, the blocked image data of the human body is output. Further, the caregiver communicates with the caregiven person employing the audio signal, and asks the caregiven person to push the authorizing switch for seeing a video showing more detailed state of the caregiven person, whereby it is possible to transmit a video signal having unblocked and detailed video and securely protect a privacy of the caregiven person.

INDUSTRIAL AVAILABILITY

As described above, the human body detecting device and the human body detecting method according to the present invention are useful for realizing a human body detection, in which a privacy of a caregiven person can be respected, and which can be employed as a life sensor, and which can provide more detailed video information to the caregiver at a distant place when abnormalities in the caregiven person are detected.

What is claimed is:

1. A body detecting device comprising:

an imaging unit that is operable to capture an image of a combination of a body and an area surrounding the body, and that is operable to output an image signal comprising image data which is a combination of data corresponding to the body and data corresponding to the area surrounding the body;

a body detecting unit that is operable to differentiate the data corresponding to the body from the data corresponding to the area surrounding the body;

a judging unit that is operable to judge whether the body is in a normal state or an abnormal state;

a normal/warning signal outputting unit that is operable to output a normal signal when said judging unit judges the body is in a normal state, and that is operable to output a warning signal when said judging unit judges that the body is in an abnormal state;

a field memory that is operable to store the combination of data corresponding to the body and data corresponding to the area surrounding the body;

a second memory that is operable to divide, and store, the data corresponding to the body into blocked data which includes data corresponding to blocks of a predetermined number of pixels and luminance; and a selector that is operable to authorize output of the combination of data corresponding to the body and data corresponding to the area surrounding the body from the field memory when said judging unit judges that the body is in an abnormal state, and that is operable to authorize output of the blocked data corresponding to the body from the second memory when said judging unit judges that the body is in a normal state.

2. The body detecting device of claim 1, further comprising:

a switch for authorizing a transmission of the image data from the field memory when reading out of the field memory is selected by the selector; and a communicator that is operable to remotely urge a person to activate the switch.

3. The body detecting device of claim 2, wherein the body is a human body.

4. A method of monitoring a body comprising:

capturing an image of a combination of a body and an area surrounding the body;

generating an image signal having image data, said image data comprising a combination of data corresponding to the body and data corresponding to the area surrounding the body;

differentiating the data corresponding to the body from the data corresponding to the area surrounding the body;

judging whether the body is in a normal state or an abnormal state;

generating a normal signal, when the body is judged to be in a normal state;

generating a warning signal, when the body is judged to be in an abnormal state;

storing the image data in a field memory;

dividing and storing the data corresponding to the body in a second memory as blocked data having a predetermined number of pixels and luminance;

reading image data from the field memory, when the judging unit judges that the body is in an abnormal state; and reading the blocked data from the second memory, when the judging unit judges that the body is in a normal state.

5. The method of claim 4, further comprising:

remotely urging a person to activate a switch;

wherein the switch authorizes transmission of the image data from the field memory when the body is judged to be in an abnormal state.

6. The method of claim 5, wherein the body is a human body.

7. A body detecting device comprising:

an imaging unit operable to generate image data;

a body detecting unit that is operable to detect a body from the image data;

a judging unit that is operable to judge whether the body is in a normal state or an abnormal state;

a normal/warning signal outputting unit that is operable to output a normal signal when said judging unit judges the body is in a normal state, and that is operable to output a warning signal when said judging unit judges that the body is in an abnormal state;

a field memory that is operable to store the image data;

a second memory that is operable to divide, and store, data corresponding to the body into blocked data of a predetermined number of pixels and luminance;

a selector that is operable to read from the field memory when said judging unit judges that the body is in an abnormal state, and that is operable to read from the second memory when said judging unit judges that the body is in a normal state; and a controller that is operable to instruct said selector to read the image data from the field memory when said judging unit judges that the body is in an abnormal state, and that is operable to instruct said selector read the blocked data from the second memory when said judging unit judges that the body is in a normal state.

8. The body detecting device of claim 7, further comprising:

a switch for authorizing a transmission of the image data from the field memory when reading out of the field memory is selected by the selector; and a communicator that is operable to remotely urge a person to activate the switch.

9. The body detecting device of claim 8, wherein the body is a human body.

10. A method of detecting a body comprising:

capturing an image of a body, and generating a corresponding image signal;

detecting the body from the image signal;

judging whether the body is in a normal state or an abnormal state;

generating a normal signal when the judging unit judges the body is in a normal state;

generating a warning signal when the judging unit judges that the body is in an abnormal state;

storing the image signal in a field memory;

dividing and storing, in a second memory, data corresponding to the body, into blocks of a predetermined number of pixels and luminance;
selecting the field memory when the judging unit judges that the body is in an abnormal state;
selecting the second memory when the judging unit judges that the body is in a normal state;
reading the field memory when the judging unit judges that the body is in an abnormal state; and
reading the second memory when the judging unit judges that the body is in a normal state.

11. The method of claim 10, further comprising:
remotely urging a person to activate a switch;
wherein the switch authorizes transmission of the image data from the field memory when the judging unit judges that the body is in an abnormal state.

12. The method of claim 11, wherein the body is a human body.

* * * * *